US012788381B2

(12) United States Patent
Barry et al.

(10) Patent No.: US 12,788,381 B2
(45) Date of Patent: Nov. 10, 2026

(54) SYSTEM FOR ENDOSCOPIC BIOPSY AND DEBULKING

(71) Applicant: American Endoscopic Innovations, LLC, Charlton, MA (US)

(72) Inventors: James P. Barry, Charlton, MA (US); Israel Franco, Chappaqua, NY (US); Michael Grasso, III, Rye, NY (US); Alfio Carroccio, Manhasset, NY (US); Thomas Ruegg, Schaffhausen (CH)

(73) Assignee: American Endoscopic Innovations, LLC, Charlton, MA (US)

( * ) Notice: Subject to any disclaimer, the term of this patent is extended or adjusted under 35 U.S.C. 154(b) by 967 days.

(21) Appl. No.: 17/177,774

(22) Filed: Feb. 17, 2021

(65) Prior Publication Data

US 2022/0257222 A1 Aug. 18, 2022

(51) Int. Cl.

| | |
|---|---|
| ***A61B 10/04*** | (2006.01) |
| ***A61B 10/02*** | (2006.01) |
| ***A61B 90/00*** | (2016.01) |

(52) U.S. Cl.

CPC .......... *A61B 10/04* (2013.01); *A61B 10/0283* (2013.01); *A61B 90/37* (2016.02); *A61B 90/39* (2016.02); *A61B 2010/0208* (2013.01); *A61B 2090/376* (2016.02); *A61B 2090/3966* (2016.02)

(58) Field of Classification Search

CPC ..... A61B 10/04; A61B 10/0283; A61B 90/37; A61B 90/39; A61B 2010/0208; A61B 2090/376; A61B 2090/3966; A61B 17/32002

See application file for complete search history.

(56) References Cited

U.S. PATENT DOCUMENTS 3,173,414 A * 3/1965 Guillant ......... A61B 17/320016 606/171
3,561,429 A * 2/1971 Jewett .................... A61B 10/04 606/171
4,014,342 A * 3/1977 Staub ..................... A61B 46/10 606/170
4,108,182 A * 8/1978 Hartman ............. A61F 9/00763 606/171
4,246,902 A * 1/1981 Martinez ............. A61F 9/00763 606/171
4,314,560 A * 2/1982 Helfgott .............. A61F 9/00763 606/171

(Continued)

FOREIGN PATENT DOCUMENTS

| | | |
|---|---|---|
| JP | 2008-500106 | 1/2008 |
| JP | 2008500106 A | 1/2008 |
| WO | WO 2005/117720 | 12/2005 |

*Primary Examiner* — Rene T Towa

(74) *Attorney, Agent, or Firm* — Fish & Richardson P.C.

(57) ABSTRACT

An endoscopic biopsy and debulking system is disclosed with a sheath having a distal end, an orifice defined on a lateral surface of the distal end, a handle disposed at a proximal end of the sheath, the handle having a connection on for attaching a hose, a suction source attached to the hose for providing negative pressure at the orifice, a cutting instrument at least partially inside the sheath and movable relative to the sheath between a first position and a cutting position, and the cutting instrument being capable of retracting or cutting tissue through the orifice in the cutting position.

22 Claims, 7 Drawing Sheets

A-A (1)

(56) References Cited

U.S. PATENT DOCUMENTS

| | | | | |
|---|---|---|---|---|
| 5,335,671 | A * | 8/1994 | Clement | A61M 1/774 600/566 |
| 6,514,215 | B1 * | 2/2003 | Ouchi | A61B 10/04 600/564 |
| 6,770,070 | B1 * | 8/2004 | Balbierz | A61B 17/00491 606/41 |
| 7,520,886 | B2 | 4/2009 | Surti | |
| 8,702,702 | B1 | 4/2014 | Edwards et al. | |
| 9,532,796 | B2 | 1/2017 | Dubois et al. | |
| 2003/0083684 | A1 * | 5/2003 | Cesarini | A61B 17/32002 606/171 |
| 2004/0162572 | A1 * | 8/2004 | Sauer | A61B 10/04 600/565 |
| 2006/0155209 | A1 * | 7/2006 | Miller | A61B 10/025 600/566 |
| 2007/0016099 | A1 * | 1/2007 | Chin | A61B 10/0275 600/564 |
| 2010/0312141 | A1 * | 12/2010 | Keast | A61B 8/12 600/567 |
| 2011/0105838 | A1 | 5/2011 | Fogel | |
| 2013/0304070 | A1 * | 11/2013 | Nelson | A61B 17/1624 606/85 |
| 2014/0088456 | A1 * | 3/2014 | Wang | A61B 10/04 600/567 |
| 2016/0262785 | A1 | 9/2016 | Dubois et al. | |
| 2019/0365404 | A1 * | 12/2019 | Ryan, Jr. | A61B 17/0218 |
| 2020/0268400 | A1 | 8/2020 | Edwards et al. | |
| 2020/0268402 | A1 | 8/2020 | Edwards et al. | |
| 2022/0257222 | A1 | 8/2022 | Barry et al. | |

* cited by examiner

SYSTEM FOR ENDOSCOPIC BIOPSY AND DEBULKING

TECHNICAL FIELD

The present invention relates to a system for endoscopic biopsy and debulking. Specifically, the present invention relates to systems and methods for providing a system that is capable of dissection, biopsy, debriding, and debulking of tissues and pathology in hollow and solid organs under direct endoscopic, radiologic and ultrasound guidance via a reciprocating or rotating cutting instrument coincident with a tubular over-structure.

BACKGROUND

Currently, to perform endoscopic biopsies and debulking, an elongated hollow cannula with a coaxial cutting forceps or wire basket or loop exiting the distal end and a proximal mechanism to actuate the cutting instrument is passed through the working channel of an endoscope. There are, however, numerous problems with this approach. At the outset, current devices are expensive, complicated, and not generally disposable.

For example, there are numerous safety issues that can arise. Excised tissue may escape the device and elude retrieval. For a reusable device, there are safety issues related to the sterile reprocessing of a narrow cannula. Finally, since the device is not fixed to the endoscope, the user must always manually control the device.

In addition, there are several control issues that arise from strictly axial access to the target organ with limited ability to retract and cut tissue found off the axis or radial to the device. For example, there is no way to retract tissue while performing the cutting operation, or to extract tissue from the patient automatically once excised. Current devices also present limited ability to take large sample or remove large masses.

There are also control issues in current systems when the cutting instrument is sized much smaller than the working channel and is free to move radially therein. Alternatively, control issues arise when the cutting instrument is unrestrained axially such that protrusion from the endoscope end tip is not fixed, or when the cutting instrument may only exit axially from the working channel and has limited means to accomplish oblique retraction or cutting.

SUMMARY

The system disclosed herein solves the problems identified above.

Cost and complexity issues may be solved by providing a modular system wherein the motor drive is detachable and reusable while the patient contact portions of the system are disposable.

The safety issues may be solved in several ways. Connecting a suction apparatus to the inner diameter of the tubular cutting blade may provide suction at the distal end of the cutting blade for positive and safe extraction of the sheared tissue and prevents escaped excised tissue. A coupling may be added at the proximal end that mates with the channel inlet port on the endoscope to fix and axially restrain the device. Further, inexpensive components may be used such that the system or components thereof may be provided sterile and disposed after one use.

The control issues may be solved in several ways. A lateral or oblique distal orifice may be provided for retraction of the tissue into the path of the cutting blade. A suction apparatus may be connected to the inner diameter of a tubular cutting blade thus providing suction at the distal orifice for tissue retraction, allowing tissue retraction or extraction during a cutting operation. Larger samples and masses may be achieved by providing a continuous reciprocating or rotary cutting action of the blade to the tissue, thus providing multiple small cuts to the tissue with continuous extraction.

Precisely sizing the protective sheath diameter to fit the working channel of the endoscope and controlling the length of the protective sheath may also stop unrestrained movements and may promote oblique retraction and cutting.

The disclosed system may have one or more new features, alone or in any combination. Such features may include the following. The system may include components being fixated to an endoscope to provide single handed control. The system may also include the component fixation being rotationally adjustable and having visible indicia of said rotational position. The system may be modular, with a disposable patient contact component and a reusable motor drive system. The system may have configurable distal tips to provide optimal tissue retraction and cutting. The system may have shape memory of the distal end to further provide oblique access to tissues. The system may have a pre-bent distal end to further provide oblique access to tissues. The system may have a shaft length specific to a mating endoscope to assure correct distal protrusion. The system, or portions thereof, may be made of disposable materials. The system may be compact, for example to minimize disposal issues. The system may be part of a larger system, and may be designed to be used with a specific endoscope.

The present teachings provide for dissection, biopsy, debriding, and debulking of tissues and pathology in hollow and solid organs under direct endoscopic, radiologic and ultrasound guidance via a reciprocating cutting instrument coincident with a tubular over-structure. Suction may be applied via the proximal end and extending to the distal end to facilitate removal of the excised tissue. Also, access to a vessel or organ may be a provided via a percutaneous route without use of the accompanying endoscope, allowing for dissection, biopsy, debulking of said vessel or harvesting of tissues.

Applications of the present teaching include:

In Urology, (urethra, prostate, bladder, ureter, and kidney), the present teachings may be used for intraluminal biopsy, removal of obstructing tissue, and improvement of patency. The present teachings may be used for harvesting tissue or tumor by itself or in conjunction with other forms of energy, such as with a laser or other form of energy capable of disintegrating a stone or calcification, to extract sediment from the urinary tract. The system may also be used percutaneously or through a sheath for biopsy, removal of tissue, or clot etc.

In GI (gastrointestinal), (esophageal, gastric, intestinal, colonic, rectal, and anal pathology) the present teachings may be used for debulking and harvesting of tissue or tumor, and also for the treatment of Barrett's esophagus and stripping of GI mucosa in the rectum, anus, colon, or other areas of the GI tract that may have some form of dysplasia, anaplasia, or tumor in sessile or flat form. The present teachings may be used in combination with a laser or other form of energy capable of disintegrating a stone, calcification, or bezoar to extract sediment or debris from the GI tract.

In ENT (ear nose and throat), the present teachings may be used to treat trans-nasal and oral lesions and conditions of the larynx, sinuses, vocal cords, and ear canal, and for biopsy, obstructing tissue removal, improvement of patency, and harvesting of tissues or tumors.

In Neurosurgery, the present teachings may be used for biopsy and removal of dedicated tissues, debris, or clots from the central and peripheral nervous system. The present teachings may also be used for intraventricular removal if tissues, debris, or clots, or transsphenoidally or transcranially for biopsy, removal of tissues, debris, or clot.

In General Surgery, the present teachings may be used as an adjunct to Laparoscopy for all intra-abdominal organs, e.g., to remove biliary lesions, liver masses, and ovarian masses. Additionally, the present teachings may be used for intraluminal biopsy, obstructing tissue removal and improvement of patency.

In Thoracic Surgery, the present teachings may be used for trans-thoracic treatment of pleural lesions, parenchymal lesions, biopsy, and removal of clot in the pleura.

In Gynecology (vagina, uterus, fallopian tube), the present teachings may be used for intraluminal biopsy, obstructing tissue removal and improvement of patency, including endometrial, myometrial, cervical, and vaginal biopsies and dissections, with or without other forms of energy. The present teachings may be used percutaneously or through a sheath for biopsy or removal of tissue or lesions of the ovaries or fallopian tubes.

In Orthopedics, the present teachings may be used as an adjunctive role in arthroscopy to harvest cells and materials, and for biopsy and removal of dedicated tissues, debris, or clot from joint spaces.

In Vascular Surgery, the present teachings may be used for debulking and removal of clots from within arteries, veins, and grafts, particularly when time has elapsed, and the clot has become more organized and firmer. The cutting apparatus and suction component allows for removal of clot in a targeted fashion when adherent to the vessel wall.

Further, in Vascular surgery, the present teachings may be used for debulking and removal of dense calcified atherosclerotic plaque in arteries or where there is recurrent hyperplastic stenosis in veins following previous treatments. In situations where angioplasty balloons or stents are not expected to be successful due to unforgiving bulk or density of the plaque, the present teachings may allow for target removal of plaque to relieve obstruction or as a preparation for subsequent angioplasty or stenting.

A POSITA would understand that the present teachings may also be used for any similar therapies of any duct or tubular structure such as the biliary system, etc.

In one aspect, an endoscopic biopsy and debulking system is disclosed with a sheath having a distal end, an orifice defined on a lateral surface of the distal end, a handle disposed at a proximal end of the sheath, the handle having a connection on for attaching a hose, a suction source attached to the hose for providing negative pressure at the orifice, a cutting instrument at least partially inside the sheath and movable relative to the sheath between a first position and a cutting position, and the cutting instrument being capable of retracting or cutting tissue through the orifice in the cutting position.

In another aspect, an endoscopic system is disclosed having a sheath having a distal end, an orifice defined on a lateral surface of the distal end, a handle disposed at a proximal end of the sheath, the handle having a connection for attaching a hose, a suction source attached to the hose for providing negative pressure at the orifice, a cutting instrument at least partially inside the sheath and movable relative to the sheath between a first position and a cutting position, the cutting instrument being capable of retracting or cutting tissue through the orifice in the cutting position, and an imaging system for visualizing the distal end of the sheath

DETAILED DESCRIPTION

Figures 1A, 1B, 1C:
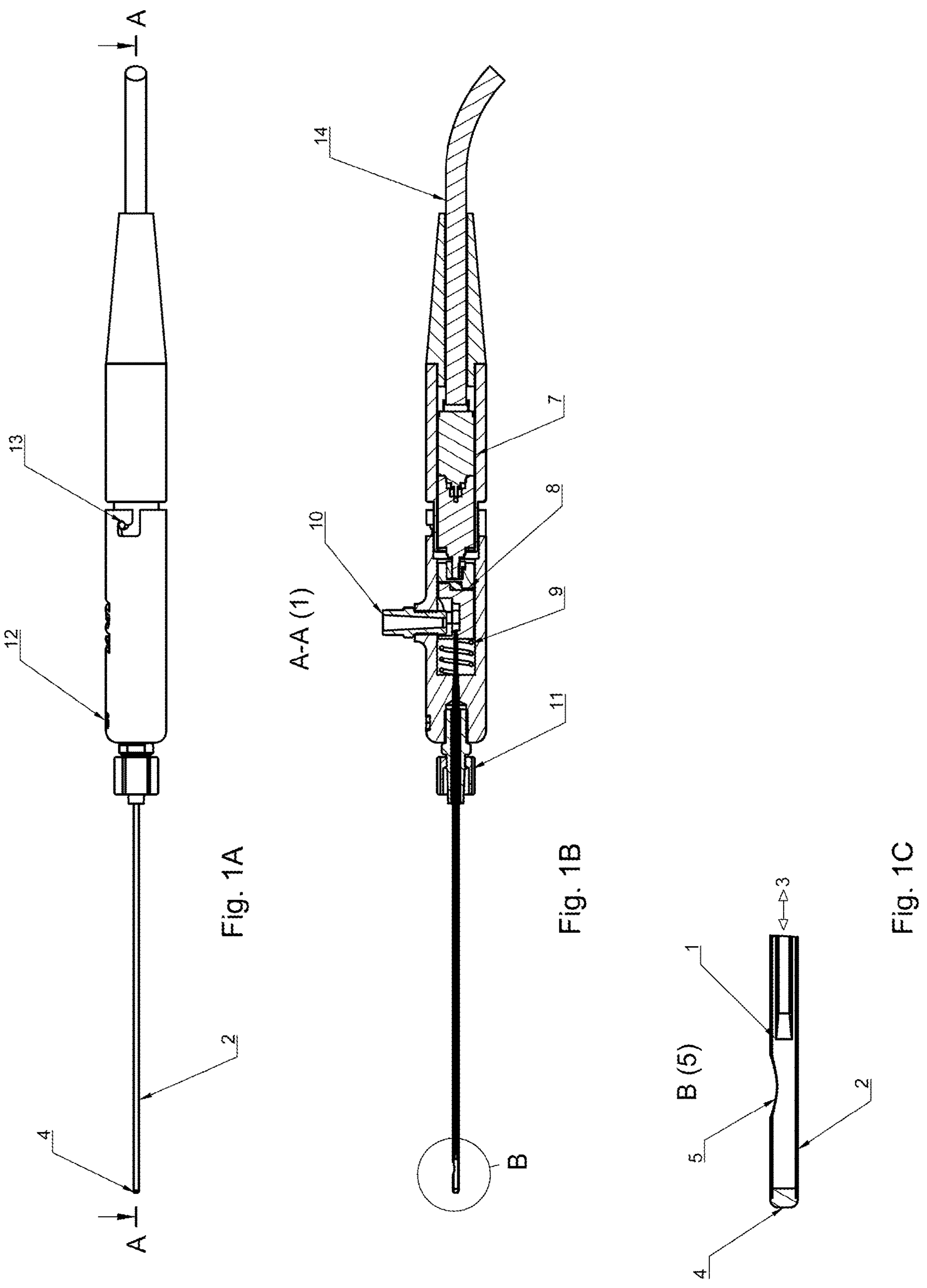
FIG. 1*a* is a bottom view of the endoscopic system with a retracted cutting blade.
FIG. 1*b* is a section, side view of the endoscopic system along the A-A axis shown in FIG. 1*a*.
FIG. 1*c* is an enlarged section view of the area of FIG. 1*b* denoted by B.
Figure 2A:
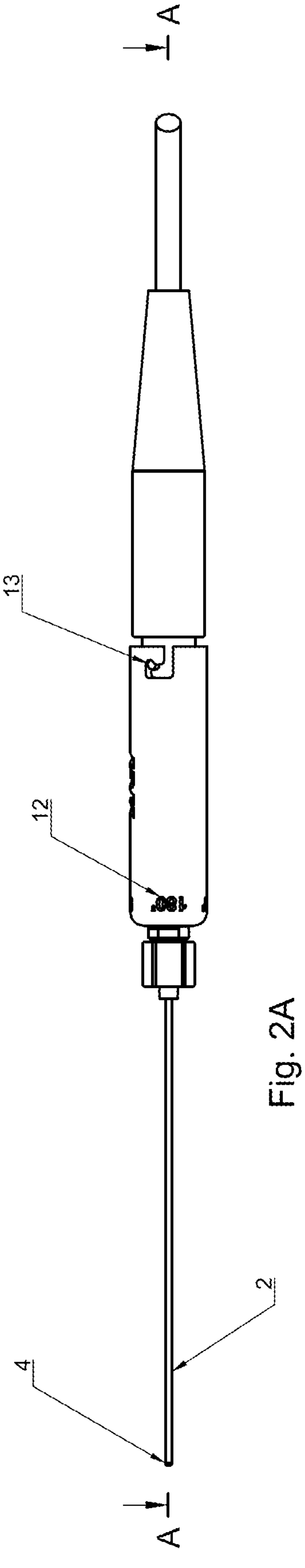
FIG. 2*a* is a bottom view of the endoscopic system with an extended cutting blade.
Figure 2B:
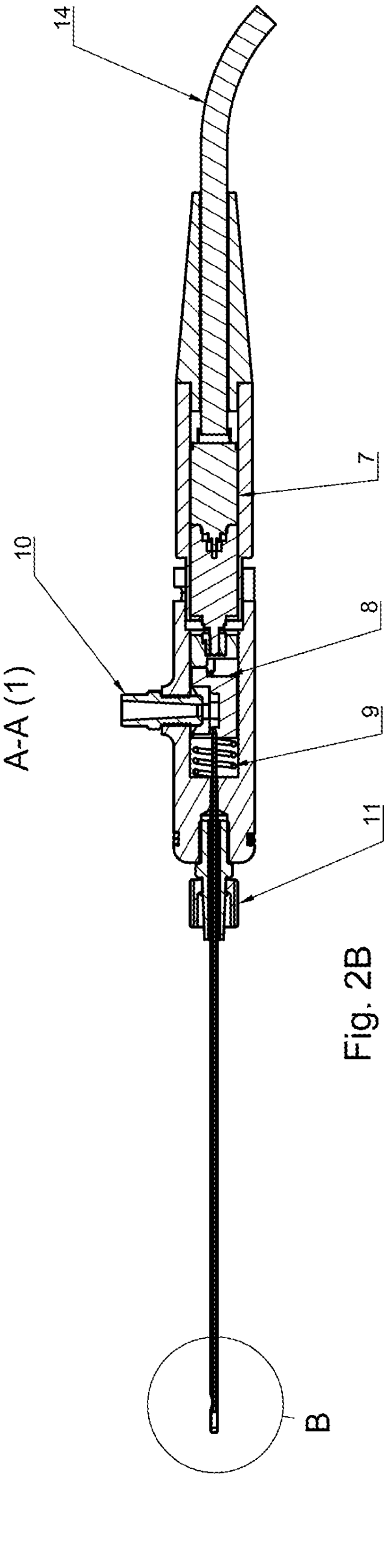
FIG. 2*b* is a section, side view of the endoscopic system along the A-A axis shown in FIG. 2*b*.
Figure 2C:
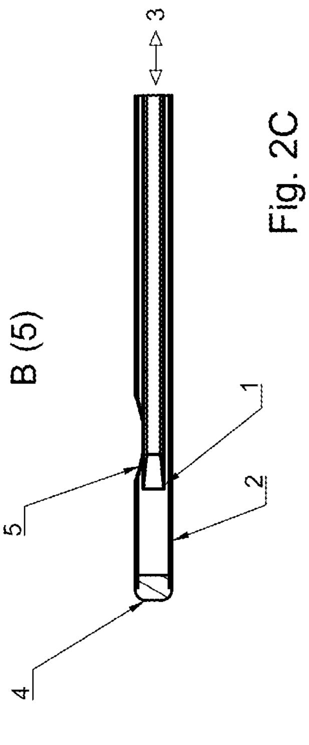
FIG. 2*c* is an enlarged section view of the area of FIG. 2*b* denoted by B.
Figure 3:
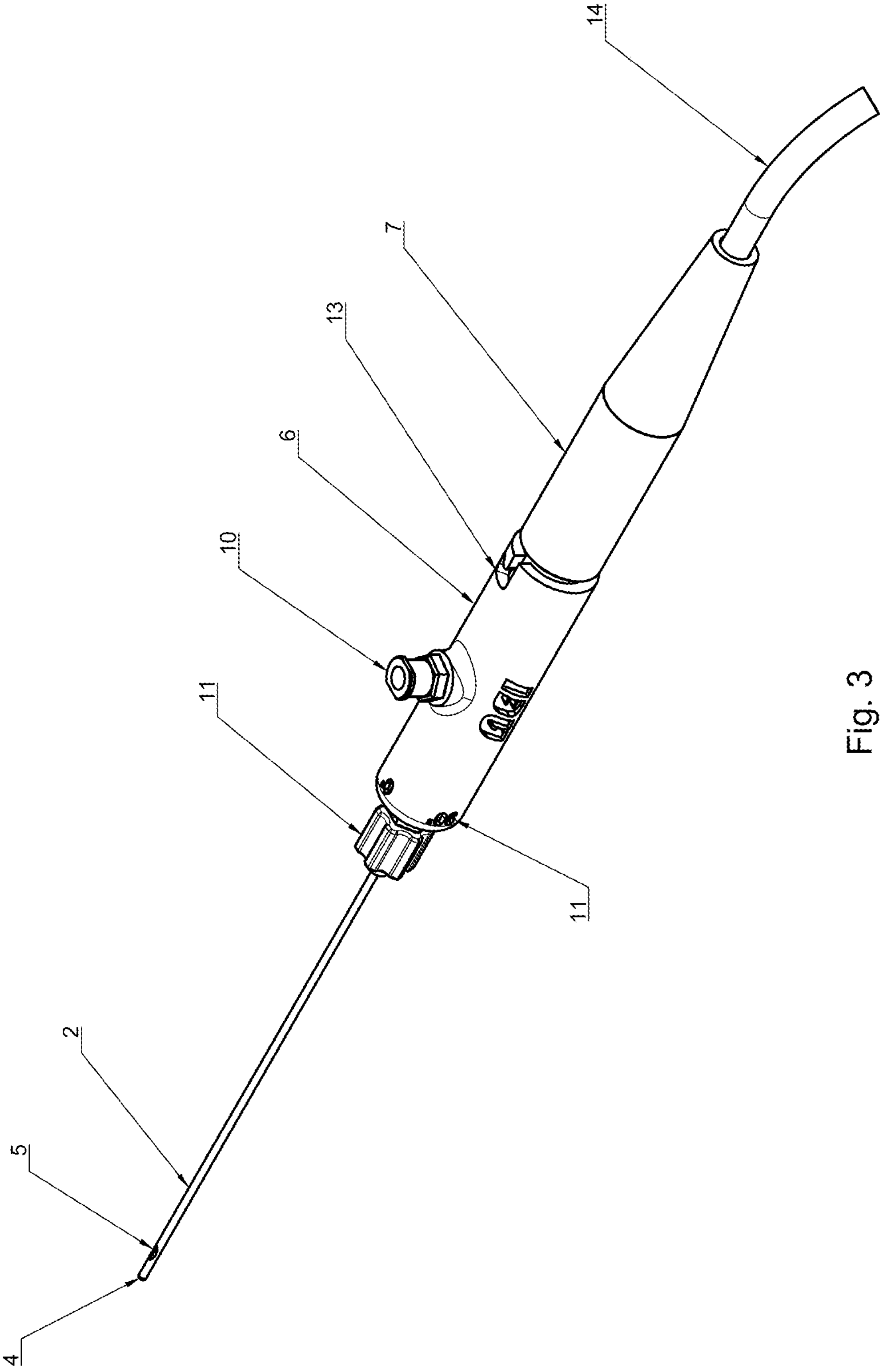
FIG. 3 is an isometric view of the endoscopic system.

An endoscopic system is shown in FIGS. 1*a*-7*c*.

An instrument 1, such as a sharpened hollow metal cannula shaped cutting blade may be disposed coaxially within a protective sheath 2. The protective sheath 2 may be of suitable length to pass through an endoscope working channel and exit the distal end of said endoscope to a prescribed distance. The instrument 1 may be capable of reciprocating axial motion 3 (see FIGS. 1*c* and 2*c*) and/or rotary motion 18 (see FIG. 6*c*) within the sheath.

The sheath 2 may have an atraumatic distal end (tip) 4 to prevent patient injury and damage to the endoscope working channel. The sheath 2 may also have a distal orifice or window 5, 17 (see FIGS. 1*c*, 2*c*, 5*c*) that provides access to the instrument 1. The distal orifice may be lateral 5 or oblique 17. The distal orifice 5, 17 may be of various different shapes, sizes, and/or directions as may be advantageous for retracting and cutting tissue and depending on the properties of the target tissue. The distal orifice 5, 17 may be placed laterally anywhere along the axis of the sheath as may be advantageous, as well as distally at any angle off axis, such as within the atraumatic tip 4. The orifice may be cut at any position from 0 to 90 degrees, typically approximately 30 deg (off axis) to 90 deg (lateral) and may be disposed along the sheath 2 or located within the atraumatic tip 4. The sheath 2 and/or the atraumatic tip 4 may be plated with a radio-opaque material (such as gold) to enhance visibility when used in conjunction with X-Ray equipment.

The cutting instrument 1 and/or the sheath 2 may be constructed of various metals including shape memory alloys (i.e., Nitinol) to improve wear characteristics and/or provide shape memory of the distal end if desired. The cutting instrument 1 and sheath 2 may be fabricated in a pre-bent distal configuration 20. The cutting instrument 1, including its tip, may be cut in any plane or multiple planes, some planes providing advantageous shearing, coring, or morcellating action.

The cutting instrument 1 and sheath 2 may be of various diameters to accommodate different scenarios. The sheath 2 may be a solid tube or a wound spring of various constructions to facilitate bending and passage through various types of endoscope lumens, including those found in flexible endoscopes.

A connection 10 to a suction source may provide negative pressure at the distal orifice 5, 17 to assist in retracting tissue into the path of the cutting blade 1. For example, the connection 10 may apply suction to the inner diameter of the instrument 1 for evacuation of tissues, fluids, and debris. The connection 10 may also be used for the introduction of fluids, under pressure or by gravity feed, typically used for clearing the endoscopic field. The connection 10 may be a Luer port.

The instrument 1 and sheath 2 may be attached to an actuator body 6 at one or more locations. This attachment may be at the proximal ends of the instrument 1 and/or sheath 2. The attachment between at least one of the instrument 1 and sheath 2, and the actuator body 6 may be permanent. The actuator body 6 may be constructed of various materials, metals or plastics and may be produced by injection molding, machining, or additive manufacturing processes. The actuator body 6, sheath 2 and cutting blade 1 and other components are preferably disposable for hygienic reasons.

Figures 6A, 6B, 6C:
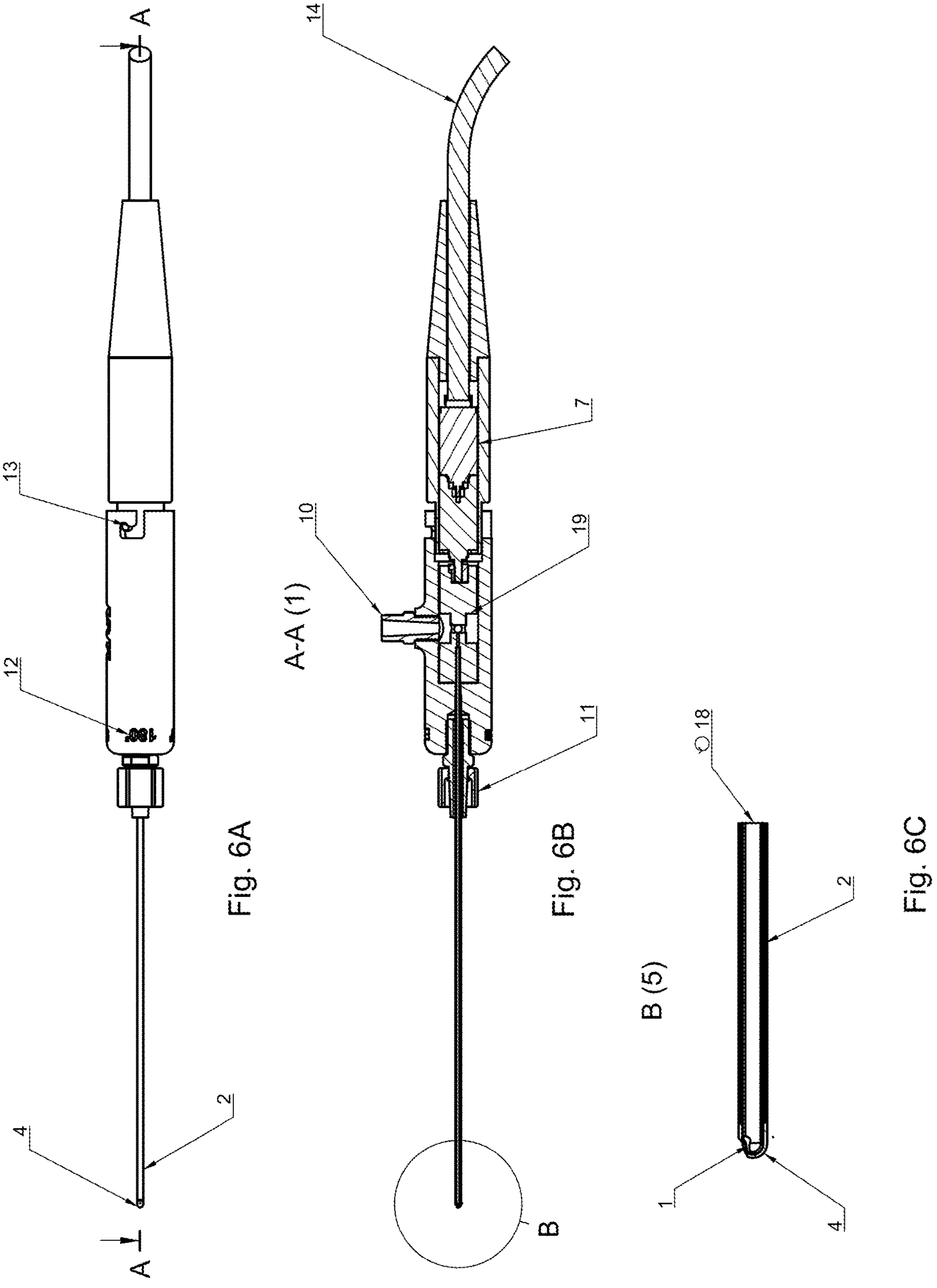
FIG. 6*a* is a bottom view of the endoscopic system with a rotary cutter.
FIG. 6*b* is a section, side view of the endoscopic system along the A-A axis shown in FIG. 6*a*.
FIG. 6*c* is an enlarged section view of the area of FIG. 6*b* denoted by B.
Figures 7A, 7B, 7C:
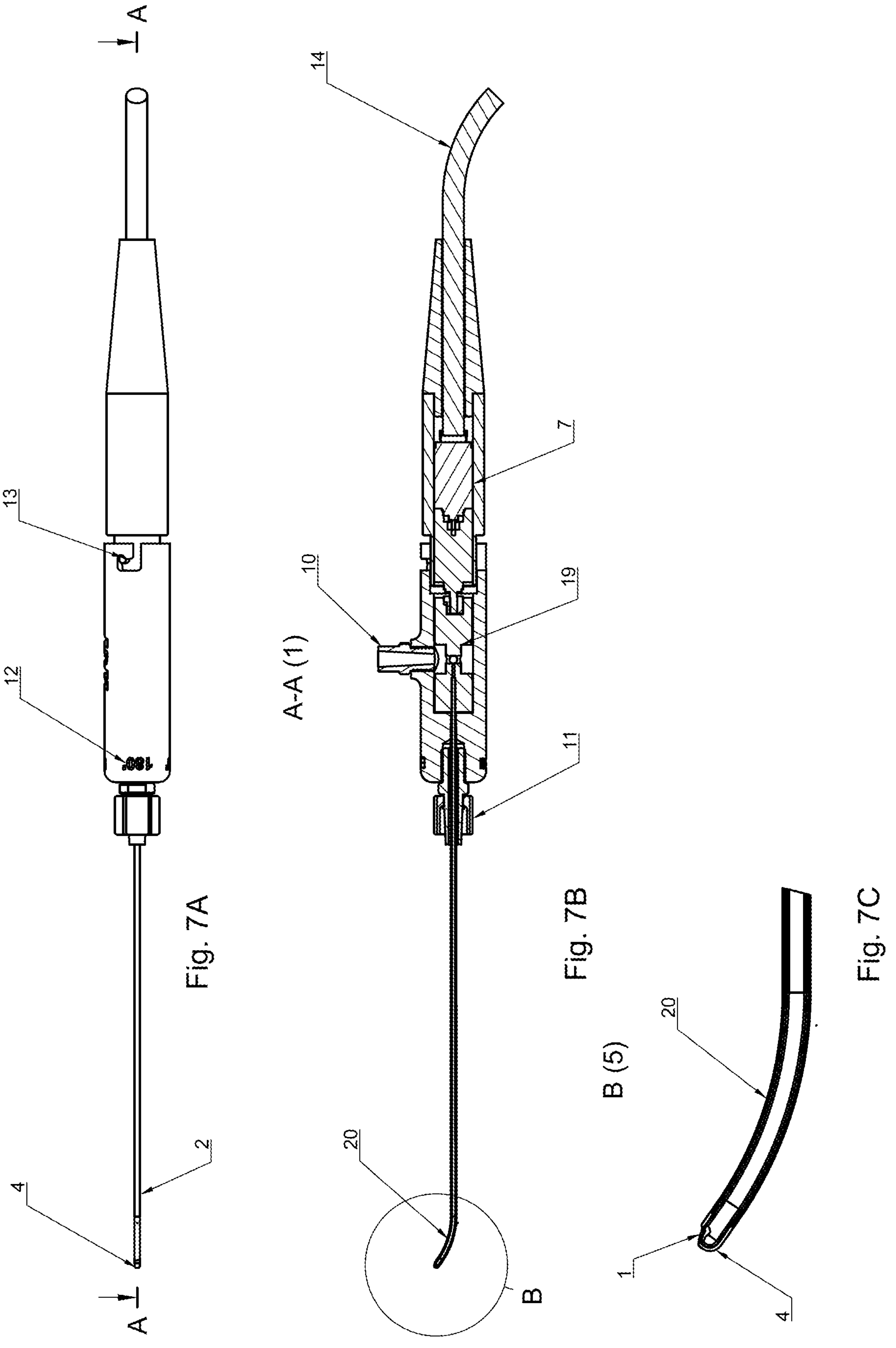
FIG. 7*a* is a bottom view of the endoscopic system with a rotary cutter and pre bent oblique distal tip.
FIG. 7*b* is a section, side view of the endoscopic system along the A-A axis shown in FIG. 7*a*.
FIG. 7*c* is an enlarged section view of the area of FIG. 7*b* denoted by B.

A detachable coupling mechanism (e.g., a bayonet coupling) 13 may be used to attach a rotary motor drive 7 to the actuator body 6. In such cases, the motor drive 7 may be reusable and the actuator body 6 may be disposable. A rotating cam 8 may translate rotary motion from the motor drive 7 to be axial motion 3 of the instrument 1. The rotating cam 8 may have various linear travel limits to provide optimal linear motion of the cutting instrument. The rotating cam 8 may have multiple lobes to provide faster or slower reciprocation of the cutting blade. A compression spring 9 may provide axial resistance against the rotating cam 8 such that the instrument 1 automatically retracts and reciprocates. As shown in FIGS. 6*b* and 6*c*, a coupling 19 may also be used to translate rotary motion from the motor drive 7 directly to the rotary action 18 of the instrument 1. A cable 14 may provide power and control signals to the motor drive 7.

Figure 4:
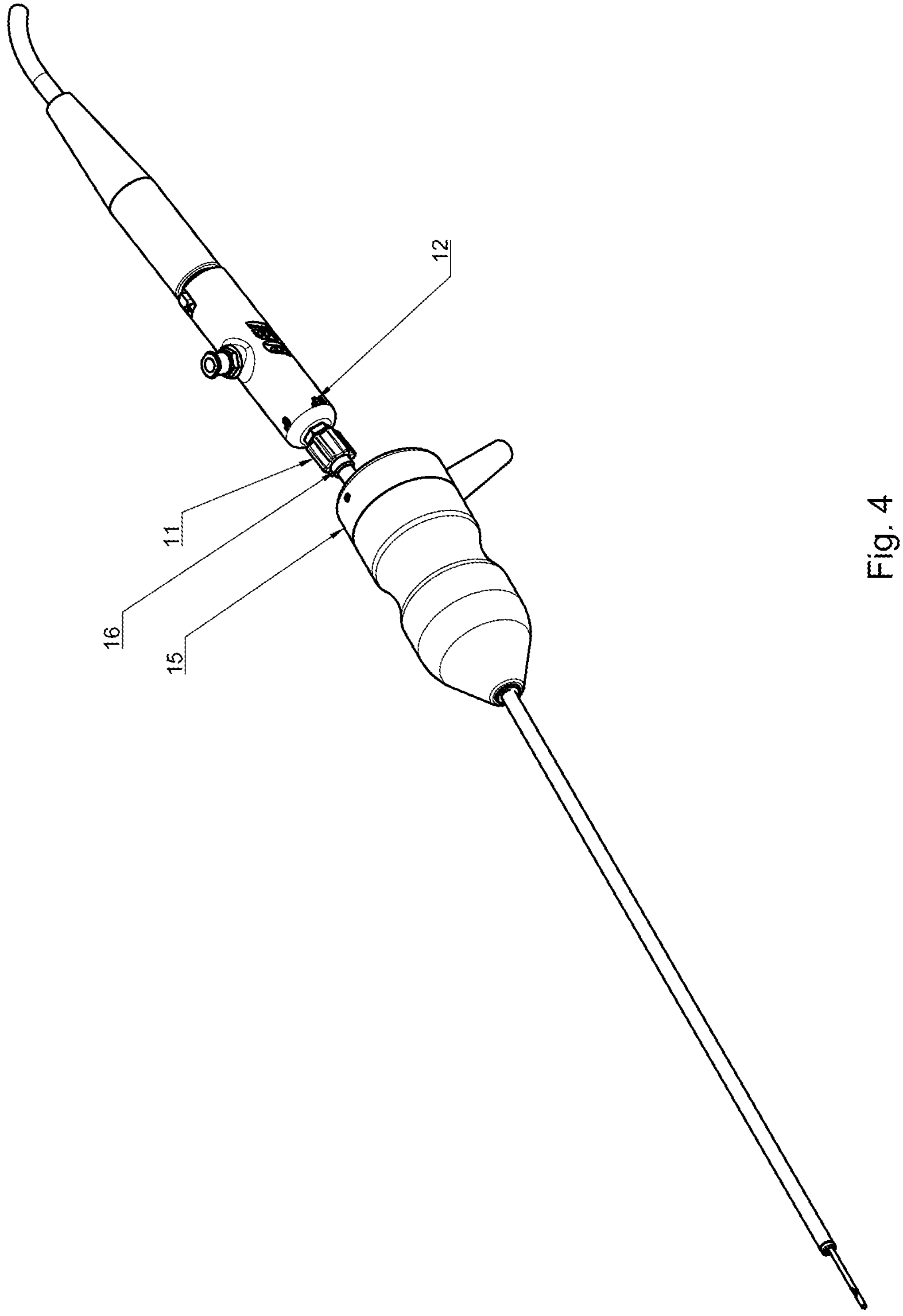
FIG. 4 is an isometric view of the endoscopic system with an endoscope.
Figure 5A:
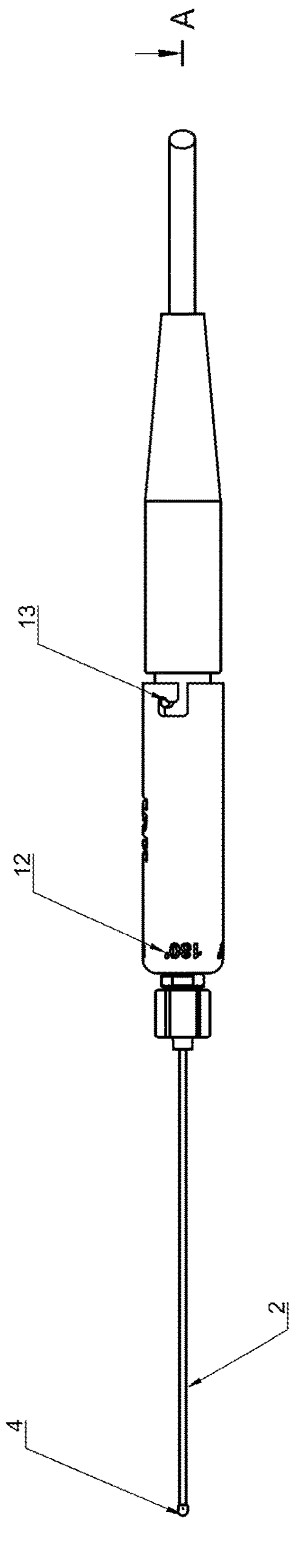
FIG. 5*a* is a bottom view of the endoscopic system with an extended cutting blade and an oblique orifice.
Figure 5B:
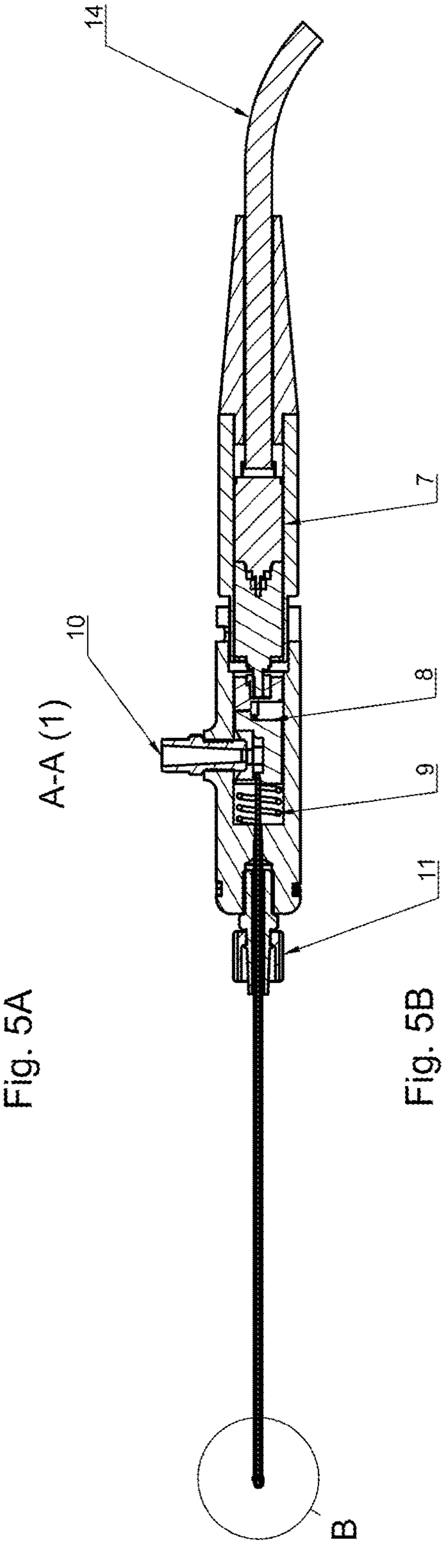
FIG. 5*b* is a section, side view of the endoscopic system along the A-A axis shown in FIG. 5*a*.
Figure 5C:
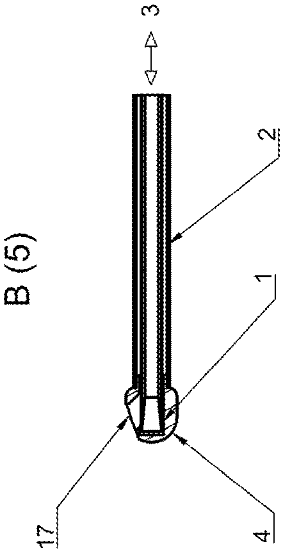
FIG. 5*c* is an enlarged section view of the area of FIG. 5*b* denoted by B.

As shown in FIG. 4, a connector 11 at the distal end of the actuator body 6 may provide an attachment to the working channel fitting 16 of an endoscope 15. This connection may be rotationally adjustable. In addition, the connector 11 and the connector 16 may be male and female Luer connectors, respectively. The cutting instrument 1 and sheath 2 may be of various lengths to accommodate different endoscopes but preferably should be specifically designed to provide exact protrusion of the sheath 2 and/or cutting instrument 1 from the distal end of said endoscope.

Indicia 12 at or near the rotationally adjustable connection may show the degrees of angular rotation of the distal end of the sheath 2 and thus the direction of the distal orifice 5, 17.

The system may be designed to interface with a cannulated endoscope. The interface with a cannulated endoscope may be designed to such that the protrusion of the sheath 2 and/or cutting instrument 1 extend at a precise length from the distal end of the endoscope. The interface may include a rotationally adjustable Luer lock fitting 11.

In operation, the actuator body 6, sheath 2, and/or cutting instrument 1 may be removed from sterile packaging. The actuator body 6 may be attached to the motor drive 7, for example via a bayonet style coupling. The sheath 2 and/or cutting instrument 1 may be inserted into the proximal endoscope working channel and passed through the channel until Luer Lock fittings 11,16 meet and are engaged. The system may be connected to a motor control system via a proximal cable 14. A suction source may be connected via the Luer port 10. The system may then be prepared for use.

During an endoscopic procedure, the distal ends of the sheath 2 and instrument 1 exit the endoscope axially, ideally within the center of the field of view, and may be placed alongside the tissue of interest via manipulation of the endoscope. The distal orifice 5, 17 may be rotationally adjusted (such as by rotating the entire device at the Luer Lock fitting 11) to coincide with the target tissue. The suction source and the motor drive 7 may be activated simultaneously or individually through use of a remote foot pedal or other like switching device. The activation of the motor drive 7 may commence a reciprocating action 3 or rotary action 18 of the cutting instrument 1. When the distal end of the system is placed in contact with the tissue of interest, the suction applied may retract said tissue into the distal orifice and the cutting blade may shear off the tissue. The depth of cut being may be controlled by the size and shape of the orifice, as well as the degree of applied suction.

Alternative uses are also considered. The system may be used extraluminally, under the direct visualization of the parent endoscope to access vessels or organs enabling dissection of tissues and removal of materials. The system may be used through an access sheath and thus directed by the sheath angulation for targeting lesions found in the outer vessel wall.

The system may also have a secondary channel for use with a guide wire. The system may then be advanced over said wire (with or without a parent endoscope attached) with the ability to rotate about the wire to debulk and bore a channel through the target anatomy. This secondary channel may also be used for the introduction of fluids, under pressure or by gravity feed, typically used for clearing the endoscopic field.

After the procedure, the sheath 2 and cutting instrument 1 may be removed from the endoscope, sheath, and/or guidewire. The actuator body 6 may be detached from the motor drive 7 and the suction source. The potentially disposable portions of the system, including but not limited to the sheath 2, cutting instrument 1, and actuator body 6, may be disposed of. Non-disposable portions, such as the motor drive 7, may be sanitized.

In compliance with the statute, the present teachings have been described in language more or less specific as to structural and methodical features. It is to be understood, however, that the present teachings are not limited to the specific features shown and described, since the systems and methods herein disclosed comprise preferred forms of putting the present teachings into effect.

For purposes of explanation and not limitation, specific details are set forth such as particular architectures, interfaces, techniques, etc. in order to provide a thorough understanding. In other instances, detailed descriptions of well-known devices, circuits, and methods are omitted so as not to obscure the description with unnecessary detail.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first", "second," etc. for different features/components of the present disclosure are only intended to distinguish the features/components from other similar features/components and not to impart any order or hierarchy to the features/components.

To aid the Patent Office and any readers of any patent issued on this application in interpreting the claims appended hereto, Applicant that it does not intend any of the claims or claim elements to invoke 35 U.S.C. 112(f) unless the words "means for" or "step for" are explicitly used in the particular claim.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. An endoscopic biopsy and debulking system comprising:

an endoscope that includes an endoscope working channel, the endoscope including a camera and a light source connected to an endoscope distal end;

a sheath that extends through the endoscope working channel, the sheath having a sheath distal end that extends beyond the endoscope distal end to a predetermined distance from the endoscope distal end and in a center of a field of view of the camera;

an orifice defined entirely on a lateral surface of the sheath distal end; a handle disposed at a proximal end of the sheath, the handle having a connection for attaching a hose;

a suction source configured to attach to the hose;

a cutting instrument that includes a cannula, the cannula having a sharpened distal end at least partially inside the sheath and movable relative to the sheath between a first position and a cutting position, the cannula defining an inner diameter that fluidly connects the sharpened distal end of the cannula with the suction source;

a motor drive connected to the handle, the motor drive including a rotating cam configured to translate rotary motion from the motor drive into axial motion of the cutting instrument;

a rotationally adjustable luer lock fitting at an interface between the endoscope and the sheath, wherein the interface is configured to control the predetermined distance, and wherein the rotationally adjustable luer lock fitting is configured to control a rotational position of the orifice with respect to the endoscope; and, a compression spring for providing axial resistance such that the cutting instrument retracts and reciprocates, wherein:

the compression spring is positioned proximally and separated from the adjustable luer lock fitting such that adjustment of the adjustable luer lock fitting does not affect compression on the compression spring, the rotationally adjustable luer lock fitting is positioned distally and separated from each of the compression spring, the connection for connecting the hose, and the rotating cam, and the connection for connecting the hose is positioned proximally from the compression spring and distally from the rotating cam, and wherein the cannula is configured to deliver a suction force from the suction source through the sharpened distal end of the cannula to generate a negative pressure at the orifice, the cutting instrument being configured to (i) retract tissue through the orifice in the first position and (ii) cut the tissue that has been retracted through the orifice in the cutting position.

2. The endoscopic system of claim 1, wherein the cutting instrument reciprocates along a longitudinal axis of the sheath to move between the first position and the cutting position.

3. The endoscopic system of claim 1, wherein the motor drive is configured to be detached from the handle and re-used, and the handle, the sheath, and the cutting instrument are single-use devices.

4. The endoscopic system of claim 1, wherein the motor drive is attached to said handle via a bayonet connection.

5. The endoscopic system of claim 1, further comprising:

an X-Ray machine for visualizing the sheath distal end; and the sheath including a radio-opaque material at the sheath distal end.

6. The endoscopic system of claim 1, further comprising a leading surface at the sheath distal end having rounded edges to be atraumatic.

7. The endoscopic system of claim 6, wherein the orifice is on the leading surface.

8. The endoscopic system of claim 1, the sheath being made of at least one of metals, and shape memory alloys.

9. The endoscopic system of claim 1, the cutting instrument being made of at least one of metals, plastics, and shape memory alloys.

10. The endoscopic system of claim 1, wherein the compression spring is positioned between the adjustable luer lock fitting and the connection for the hose.

11. The endoscopic system of claim 10, wherein the rotating cam is positioned proximally from the connection for connecting the hose and distally from the motor drive.

12. The endoscopic system of claim 1, further comprising a symbol on the handle for providing an indication of a rotational position of the orifice on the sheath distal end.

13. The endoscopic system of claim 1, further comprising a monitor for visualizing the sheath distal end, wherein the sheath distal end is positioned at a fixed distance from the endoscope distal end and at a center of a field of view of the camera.

14. The endoscopic system of claim 1, wherein the sheath and the cutting instrument are flexible.

15. The endoscopic system of claim 1, wherein at least one of the sheath and the cutting instrument are semi-rigid.

16. The endoscopic system of claim 1, wherein the sheath, the cutting instrument, and the handle are disposable.

17. The system of claim 1, further comprising an endoscope connector and a handle connector configured to engage with each other and control the extension of the sheath beyond the endoscope distal end.

18. The system of claim 1, wherein the orifice is sized and shaped on the sheath to allow cuts at an off-axis position.

19. The endoscopic system of claim 1, the cutting instrument and sheath being made of shape memory alloys.

20. An endoscopic system comprising:
a sheath comprising shape memory alloys that extends through an endoscopic working channel, the sheath having a sheath distal end that extends beyond an endoscope distal end;
an orifice defined on a lateral surface of the sheath and spaced apart from the sheath distal end;
a handle disposed at a proximal end of the sheath, the handle having a connection for attaching a hose and a connection for attaching a motor drive; a suction source attached to the hose for providing negative pressure at the orifice;
a cutting instrument comprising shape memory alloys at least partially inside the sheath and movable relative to the sheath between a first position and a cutting position;
a motor drive connected to the handle, the motor drive including a rotating cam configured to translate rotary motion from the motor drive into axial motion of the cutting instrument the cutting instrument being capable of retracting or cutting tissue through the orifice in the cutting position;
an imaging system connected to the endoscope distal end for visualizing the distal end of the sheath;
a rotationally adjustable luer lock fitting at an interface between the imaging system and the sheath, wherein the rotationally adjustable luer lock fitting is configured to control a rotational position of the orifice with respect to the endoscope distal end; and
a compression spring for providing axial resistance such that the cutting instrument retracts and reciprocates,
wherein:
the compression spring is positioned proximally and separated from the adjustable luer lock fitting such that adjustment of the adjustable luer lock fitting does not affect compression on the compression spring,
the rotationally adjustable luer lock fitting is positioned distally and separated from each of the compression spring, the connection for connecting the hose, and the rotating cam, and
the connection for connecting the hose is positioned proximally from the compression spring and distally from the rotating cam.

21. The endoscopic system of claim 20, wherein the distal end of the sheath extends to a predetermined distance from the endoscope distal end and is positioned in a center of a field of view of the imaging system.

22. The endoscopic system of claim 21, further comprising a compression spring for providing axial resistance such that the cutting instrument retracts and reciprocates, the compression spring is positioned proximally and separated from the adjustable luer lock fitting such that adjustment of the adjustable luer lock fitting does not impact compression on the compression spring.

* * * * *